(12) United States Patent
Hoshino et al.

(10) Patent No.: US 6,352,685 B2
(45) Date of Patent: Mar. 5, 2002

(54) EXTERNAL PREPARATION FOR SKIN

(75) Inventors: Taku Hoshino; Osamu Sakata; Masahiro Moriyama, all of Tokyo; Yoshihiro Higuchi, Chiba, all of (JP)

(73) Assignees: Kosé Corporation, Tokyo; Shiratori Pharmaceutical Co., Ltd., Chiba, both of (JP)

( * ) Notice: Subject to any disclaimer, the term of this patent is extended or adjusted under 35 U.S.C. 154(b) by 0 days.

(21) Appl. No.: 09/740,859

(22) Filed: Dec. 22, 2000

(30) Foreign Application Priority Data

Dec. 24, 1999 (JP) .......................................... 11-367587
Feb. 7, 2000 (JP) .......................................... 12-029348

(51) Int. Cl.⁷ .......................... A61K 7/42; A61K 6/00; A61K 35/78; A01N 37/02
(52) U.S. Cl. ........................ 424/59; 424/757; 424/401; 514/547
(58) Field of Search .......................... 424/59, 757, 401; 514/547

(56) References Cited

U.S. PATENT DOCUMENTS

| | | | |
|---|---|---|---|
| 5,078,989 A | * | 1/1992 | Ando et al. |
| 5,618,545 A | * | 4/1997 | Orita et al. |
| 5,728,733 A | * | 3/1998 | Ptchelintsev |
| 6,120,782 A | * | 9/2000 | Mansouri |
| 6,242,092 B1 | * | 6/2001 | Katsuyama et al. |

FOREIGN PATENT DOCUMENTS

| | | | |
|---|---|---|---|
| EP | WO 8300433 | * | 2/1983 |
| FR | 2309210 | * | 12/1976 |

OTHER PUBLICATIONS

The Home of Siamese Herbal Products, *Pueraria mirifica* (wysiwyg://97/http://www.trisiam.com/pueraria.htm).*
Sher Natural Introduction, "Breakthrough Discovery in Natural Breast Enhancement", (http:///www.all–nautralbreasts.net/sher.htm).*

* cited by examiner

Primary Examiner—Christopher R. Tate
Assistant Examiner—Randall Winston
(74) Attorney, Agent, or Firm—Fei-Fei Chao; Venable, Baetjer, Howard & Civiletti, LLP

(57) ABSTRACT

The object of the invention is to provide a new external preparation for skin having high melanine formation inhibition and also anti-aging effect, and desired drug effect can be obtained without degradation in a pharmaceutical preparation.

The external preparation for skin includes the extract of *Pueraria mirifica* in conbination with an active ingredient selected from the group consisting of a whitening agent, an anti-oxidant, an anti-inflammation agent, an ultraviolet-ray shielding ingredient, a cell activation agent and humectant.

20 Claims, No Drawings

EXTERNAL PREPARATION FOR SKIN

This application claims the priority of the Japanese Patent Application No. 11-367587 filed on Dec. 24, 1999 and Japanese Patent Application No. 2000-29348 filed on Feb. 7, 2000, which are incorporated herein by reference.

FIELD OF THE INVENTION

The present invention relates to an external preparation for skin including an extract from a particular plant, and more particularly, to an improvement of anti-aging effect and whitening effect thereof.

BACKGROUND OF THE INVENTION

Generally, the external preparations for skin such as milky lotions, creams, lotions, packs, detergents, dispersion solutions, ointments, liquids for external use are including various active ingredients, to perform specified drug effect.

For example, external preparations for whitening include whitening ingredients of ascorbic acid, glutathione and hydroquinon etc., to prevent phenomenon of darkening caused by sunburn, brown spot and freckle etc. caused by pigmentation.

Also, cell activation agents of vitamin A, soybean extract and seaweed extract etc. are compounded in the external preparation for skin for the purpose of an anti-aging effect, to improve wrinkle, slack of skin caused by aging, ultraviolet rays exposure etc.

However, in the prior arts, the effects of the component for whitening or anti-aging were not sufficient. And, these components may be degraded in pharmaceutical preparation. Because of this, these conventional components are not sufficient to demonstrate desired drug effect. Therefore, improvements of these and new active ingredients have been desired.

SUMMARY OF THE INVENTION

The object of the invention is to provide better whitening or anti-aging effect by a high safety plant extract.

The present inventors have been conducted a search for natural components that have excellent drug effect and can use as an active ingredient of external preparation for skin, and found an extract from *Pueraria mirifica*, that is a plant in Southeast Asia, has high melanine formation inhibition and also anti-aging effect. Furthermore, the extract is effective when it is compounded in external preparation for skin as a whitening component or an anti-aging component. Also, excellent effects are obtained when other active ingredients are compounded with the extract. The inventors have completed the invention based on this finding.

Namely, an external preparation for skin according to the present invention includes an extract of *Pueraria mirifica*.

Also, in said external preparation for skin, the extract of *Pueraria mirifica* is preferably compounded as a whitening component.

Also, an external preparation for whitening according to the present invention comprises;
(A) extract of *Pueraria mirifica*;
(B) one or more active ingredient selected from the group consisting of a whitening agents, an anti-oxidant, an anti-inflammation agent and an ultraviolet-ray shielding ingredient.

Also, in said external preparation for skin, the extract of *Pueraria mirifica* is preferably compounded as an anti-aging component.

Also an external preparation for anti-aging according to the present invention includes the followings;
(A) the extract of *Pueraria mirifica*;
(B) one or more effective ingredient selected from the group consisting of a cell activation agent, an anti-oxidant, a humectant, and an ultraviolet-ray shielding ingredient.

DETAILED DESCRIPTION OF THE PREFERRED EMBODIMENT

*Pueraria mirifica*, of which extract is used as an active ingredient in the invention, is a plant grows in Southeast Asia. The plant belongs to *Legume lobata* and called Kwaao Khruea in Thailand. *Pueraria mirifica* includes various isoflavone derivatives that have female hormone effect. Therefore, it has been used as a Thailand medicine, private spice, herb, traditional medicine etc. heretofore.

The extract of the above plant used for the invention is obtained by extracting a dried root lump of said plant by using a proper extraction solvent. The method for preparation is not restricted but especially prepared by extracting under low temperature or room temperature to warming by using a proper solvent.

As for extraction solvent used in the invention, examples are as follows;
water; lower alcohol such as methyl alcohol, ethyl alcohol; liquid polyhydric alcohol such as glycerol, propylene glycol, 1,3-butylene glycol. One or more of these can be used for the extraction solvents.

Also, the example of the preferable extraction method is as follows. The extraction from *Pueraria mirifica* is carried out for 1 to 5 days with room temperature by 0~100 v/v % water content ethyl alcohol or 1,3-butylene glycol. This extract is filtered. The filtrate thus obtained was allowed for around 1 week for aging. The result was filtered again.

The compounding quantity of *Pueraria mirifica* extract in the external preparation for skin of this invention is preferably 0.00001~5 wt % (hereinafter indicated "%" only) as the dried solid in the composition. In the case where it is used as a whitening component, the compounding amount is more preferably 0.03~2%. In the case where it is used as an anti-aging component, the compounding amount is more preferably 0.0001~2%. Said plant extract can be stably compounded in this range and show a high effect. In the case where the extract is used as liquid, as long as the content of the dried solid in extract is in above range in the external preparation, the concentration is not restricted.

The *Pueraria mirifica* extract of this invention can be compounded with the various bases of usual external preparation for skin in accordance with common methods. The external preparation for skin can show excellent effect, by compounding with other active ingredients.

As for the active ingredients ((B) component) in combination with the *Pueraria mirifica* extract ((A) component), examples are as follows. In the case of a whitening use, the active ingredients may be other whitening agents, antioxidants, antiinflammation agents, ultraviolet-ray shielding ingredients etc. In the case of an anti-aging use, the active ingredient is a cell activation agent, anti-oxidants, humectants, ultraviolet-ray shielding ingredients etc. These concrete active ingredients are shown below, respectively.

Whitening Agent

As for whitening agent used in the invention, examples are as follows; vitamin C, its derivatives and salts thereof, placenta extract, licorice extract, coix seed extract, scutellaria root extract, seaweed extract etc. The whitening agents are not restricted as long as which has a whitening effect. In these whitening agents, vitamin C, its derivatives and salts thereof, and placenta extracts are preferable.

Anti-Oxidant

As for anti-oxidant used in the invention, examples are as follows; vitamins B, its derivatives and salts thereof, vitamin E, its derivatives and salts thereof, dibutylhydroxytoluene, dibutyl hydroxyanisol, mannitol, carotenoid such as astaxanthine, plant extract including flavonoid such as quercetin, quercitrin, ginkgo extract, scutellaria root extract, balm mint extract, saxifrage extract, Siberian ginseng extract, and Alnus firma Siebold. et Zucc. extract. In these anti-oxidant, vitamin E, its derivatives and salts thereof are preferable.

Anti-Inflammation Agent

As for anti-inflammation agent used in the invention, examples are as follows; glycyrrhizinic acid, glycyrrhetinic acid, those derivatives and those salts, aloe extract, perilla extract, mugwort extract and matricaria extract. In these anti-inflammation agents, glycyrrhizinic acid, glycyrrhetinic acid, those derivatives and those salts are preferable.

Ultraviolet-Ray Shielding Agent

As for ultraviolet-rays shielding agent used in the invention, examples are as follows; 2-ethylhexyl-p-methoxy cinnamate, oxybenzone, 4-tert-butyl-4'-methoxy dibenzoylmethane, titanium oxide, micronized particle titanium oxide, and zinc oxide. In these ultraviolet-ray shielding ingredients, 2-ethylhexyl-p-methoxy cinnamate, titanium oxide, micronized particle titanium oxide and zinc oxide are preferable.

Cell Activation Agent

As for cell activation agent used in the invention, examples are as follows; vitamin A, its derivatives and those salts, vitamin C, its derivatives and those salts, estradiol, placenta extract, yeast extract, apricot extract, plant extract including AHA such as lime extract and raspberry extract, asparagus extract, almond extract, soybean extract, centella extract, tomato extract, malt root extract and seaweed extract. In these cell activation agents, vitamin A, its derivatives and those salts, and estradiol are preferable.

Humectant

As for humectant used in the invention, examples are as follows; amino acid, its derivatives and those salts, mucopolysaccharide, its derivatives and those salts, phospholipid and its derivatives, sweet hydrangea leaf extract, aloe extract, cactus extract, coltsfoot extract, quince seed extract, glycerol, and 1,3-butylene glycol. In these humectant, amino acid, its derivatives and those salts, phospholipid and its derivatives, glycerol and 1,3-butylene glycol etc. are preferable.

The compounding amount of the active ingredient of above (B) component in the external preparation for skin of this invention differs depend on the kind of active ingredient. However, the compounding amount is preferably in the range shown below. In the case of compounding the active ingredients with the extract of *Pueraria mirifica* as (A) component in the range, it does not influence on stability with time and shows higher whitening effect and anti-aging effect.

In the case of the external preparation for whitening of this invention, other whitening agents as (B) component can be compounded in an amount of 0.00001~10%, preferably 0.0001~5% in the composition. In the case of using the placenta extract or various plant extracts in liquid, the compounding amount should be in the range as dried solid. This range shows excellent whitening effect and fine feel of use.

In the case of the whitening external preparation of this invention, the anti-inflammation agent as (B) component can be compounded in an amount of 0.00001~5%, preferably 0.0001~3% in the composition. In the case of using various plant extracts in liquid, the compounding amount should be in the range as dried solid. This range shows an excellent antiinflammation effect and excellent whitening effect.

In the case of the anti-aging external preparation for skin of the invention, the cell activation agent as (B) component can be compounded in an amount of 0.00001~10%, preferably 0.0001~5% in the composition. In the case of using the placenta extract or various plant extracts in liquid, the compounding amount should be in the range as dried solid. This range shows excellent cell activation effect and excellent antiaging effect.

In the case of the anti-aging external preparation of this invention, the humectants as (B) component can be compounded in an amount of 0.00001~5%, preferably 0.0001~3% in the composition. In the case of using various plant extracts in liquid, the compounding amount should be in the range as a dried solid. This range shows excellent moisturizing effect and excellent anti-aging effect.

Also, in the case of either of the external preparations of this invention, the anti-oxidants as (B) component can be compounded in an amount of 0.00001~5%, preferably 0.0001~3% in the composition. In the case of using various plant extracts in liquid, the compounding amount should be in the range as dried solid. This range shows excellent anti-oxidant effect, excellent anti-aging effect and whitening effect.

Also, in the case of either of the external preparations of this invention, the ultraviolet-ray shielding agents as (B) component can be compounded in an amount of 0.0001~20%, preferably 0.001~10% in the composition. This range shows excellent ultraviolet-ray shielding effect, excellent anti-aging effect and whitening effect.

One or more of various kinds of (B) component can be combined to use.

The external preparation for skin including above (A) component and (B) component can be prepared in accordance with a common method. Namely, (A) component and (B) component are compounded in the bases of various state which can be used in usual external preparation for skin.

As for concrete product in connection with the external preparation for skin of the invention, examples are as follows. Cosmetics and medical external preparation such as a milky lotion, cream, lotion, pack, detergent, makeup cosmetic, dispersion solution and ointment.

The external preparation for skin of this invention can include components, that are usually used in the external preparation for skin such as the cosmetics and medical external preparation, other than the above indispensable components. Followings are examples; purified water, lower alcohol, polyhydric alcohol, oily components, powders, surface active agents, thickeners, color materials, antiseptics, humectants and perfume etc.

In the following, this invention is explained in detail by reference examples, test examples and also embodiments. This invention is not restricted to these.

REFERENCE EXAMPLE 1

Preparation of *Pueraria mirifica* Extract

Each 100 mL of purified water, 50% ethyl alcohol solution, and ethyl alcohol was added to 10 g of dried root lumps of *Pueraria mirifica*, as shown in TABLE 1. The mixtures were extracted for 3 days under room temperature and each plant extracts was obtained by filtration. The dried solid of these extracts shown in TABLE 1.

TABLE 1

| EXTRACT | DRIED SOLID (%) |
|---|---|
| (1) purified water extract | 4.2 |
| (2) 50% ethyl alcohol extract | 2.1 |
| (3) ethyl alcohol extract | 1.2 |

REFERENCE EXAMPLE 2

Preparation of *Pueraria mirifica* Extract (2)

Each 50 ml of purified water and 50% ethyl alcohol solution was added to 10 g of dried root of *Pueraria mirifica*, respectively as shown in TABLE 2. These mixtures were extracted 3 times at 50° C. Each plant extracts were obtained by filtering. The dried solid of these extracts are shown in TABLE 2.

TABLE 2

| EXTRACT | DRIED SOLID (%) |
|---|---|
| (1) purified water extract (warming) | 5.6 |
| (2) 50% ethyl alcohol extract (warming) | 2.9 |

REFERENCE EXAMPLE 3

Preparation of Coix Seed Extract 100 mL of ethyl alcohol solution (water content 70 vol %) was added to 10 g of coix seed (Pharmaceutical Codex of Japan). The mixture was extracted for 3 days in room temperature. The coix seed extract was obtained by filtration. The dried solid of the coix seed extract was 0.8%.

REFERENCE EXAMPLE 4

Preparation of Soybean Extract 100 ml of ethyl alcohol solution (water content 70 vol %) was added to 10 g of soybeans seeds. The mixture was extracted for 3 days in room temperature. The soybean extract was obtained by filtration. The dried solid of the soybean extract was 0.5%.

WHITENING TEST-1

Inhibition for Melanine Formation and Cell Survival Rate Test by Cell Culturing

A test was conducted by using B16 melanoma cultured cell of mouse origin. A proper quantity of culture medium was put in 2 sheets of 6 holes laboratory dish. B16 melanoma cell was inoculated to these culture mediums. These laboratory dishes were stored in the temperature of 37° C. under the environment of 5% carbon dioxide concentration. Next morning, the purified water extract, 50% ethyl alcohol solution extract and ethyl alcohol extract of *Pueraria mirifica*, these were obtained by Reference example 1, were added to the culture medium. The concentrations of these extracts were prepared so these final concentrations as to be 0(contrast), 300, 500, and 1000 µg/mL respectively and the culture mediums were mixed. The culture mediums were exchanged after the incubation of 5 days. The same solution of the first was added again. Next morning, the culture mediums were eliminated. The cell was retrieved after washing with phosphoric acid buffer solution for one sheet of the laboratory dishes. The whitening effect of B16 melanoma cultured cell was evaluated with the following standard. The coix seed extract was used as a comparative example, which has already been known as a melanine formation inhibitor, and the same test was conducted.

(Whitening effect criterion)

| <Interpretation> | <contents> |
|---|---|
| ++ | Extremely white in contrast with reference |
| + | Obviously white in contrast with reference |
| ± | White a little in contrast with reference |
| − | Black as same as reference |

The cell of another laboratory dish was fixed with formalin and dyed by adding 1% crystal violet solution. The survival cell rate for each subject concentration was measured with MONOCELLATER (OLYMPUS OPTICAL COMPANY). The measured result of the survival rate and also the whitening effect were shown in TABLE 3.

TABLE 3

| EXTRACT | | 300 | 500 | 1000 |
|---|---|---|---|---|
| (1) purified water extract | Whitening effect | ± | ± | + |
| | Survival rate(%) | 100 | 100 | 100 |
| (2) 50% ethyl alcohol extract | Whitening effect | ± | ± | + |
| | Survival rate(%) | 96 | 95 | 93 |
| (3) ethyl alcohol extract | Whitening effect | ± | ± | + |
| | Survival rate(%) | 94 | 93 | 88 |
| coix extract | Whitening effect | — | — | |
| | Survival rate(%) | 100 | 100 | 99 |

(1)–(3): Product by Reference example 1
Coix extract: Product by Reference example 3

As is clear from the result of TABLE 3, said plant extracts have high inhibition ability for melanine formation. Also, the toxicity to B16 melanoma cultured cell is in low level. Accordingly, said plant extract demonstrates extremely excellent melanine formation inhibition, by applying this on skin and also inhibits brownig, brown spots, freckle etc. of skin by sunburn, effectively.

EXAMPLE 1-1

Whitening Cream

The whitening creams were prepared in accordance with the composition shown in TABLE 4 and process. The whitening effect of *Pueraria mirifica* was studied. TABLE 4 shows the result.

TABLE 4

| | Present invention | | | Comparison | |
|---|---|---|---|---|---|
| Composition | 1 | 2 | 3 | 1 | 2 |
| (1)beeswax | 6.0 | 6.0 | 6.0 | 6.0 | 6.0 |
| (2)cetanol | 5.0 | 5.0 | 5.0 | 5.0 | 5.0 |
| (3)reduced lanolin | 5.0 | 5.0 | 5.0 | 5.0 | 5.0 |
| (4)squalan | 30.0 | 30.0 | 30.0 | 30.0 | 30.0 |
| (5)lipophilic glyceryl monostearate | 4.0 | 4.0 | 4.0 | 4.0 | 4.0 |
| (6)polyoxyethylene sorbitan monolaulate (20 E.O.) | 2.0 | 2.0 | 2.0 | 2.0 | 2.0 |

TABLE 4-continued

|  | Present invention | | | Comparison | |
|---|---|---|---|---|---|
| Composition | 1 | 2 | 3 | 1 | 2 |
| (7)purified water extract of *Pueraria mirifica* | 5.0 | — | — | — | — |
| (8)50% ethyl alcohol extract of *Pueraria mirifica* | — | 5.0 | — | — | — |
| (9)ethyl alcohol extract of *Pueraria mirifica* | — | — | 5.0 | — | — |
| (10)L-ascorbyl magnesium phosphate | — | — | — | 3.0 | — |
| (11)antiseptics | q.s. | q.s. | q.s. | q.s. | q.s. |
| (12)perfume | q.s. | q.s. | q.s. | q.s. | q.s. |
| (13)purified water | balance | balance | balance | balance | balance |
| Whitening effect — effective | 11 | 10 | 14 | 7 | 0 |
| — slightly effective | 3 | 4 | 1 | 8 | 2 |
| — null | 1 | 1 | 0 | 0 | 13 |

(7)–(9)product by Reference example 1
(10)Product of NIKKO CHEMICALS COMPANY (Process)
A. The components (1)–(6) and (11) were mixed, heated and kept to 70° C.
B. A part of the component (13) was heated and kept to 70° C.
C. Part (B) was added to Part (A). The components (7)–(9), (10) dissolved by other part of (13), and (12) were mixed and cooled to obtain the cream.

(Test Method)

15 panels of 27–54 years old women were joined to the test for one subject cream. Twice in a day, in the morning and night, they applied proper quantity of subject cream to their faces after washing for 12 weeks. The whitening effect by application was evaluated by the following standard.

(Evaluation standard)

| <Evaluation> | <contents> |
|---|---|
| Effective | Dark of skin becomes inconspicuous. |
| Slightly Effective | Dark of skin becomes a little inconspicuous. |
| Null | No change with before use |

By applying the external preparations compounding the purified water extract, the 50% ethyl alcohol extract and the ethyl alcohol extract of *Pueraria mirifica* on skin, it is possible to prevent or improve "dark" of skin etc. and make skin beautiful as shown in TABLE 4.

EXAMPLE 1-2

Whitening Cream

The cream was prepared in accordance with composition shown in TABLE 5 and following process. A whitening effect of creams which included 50% ethyl alcohol extract in combination with a whitening agent, an anti-oxidant, an anti-inflammation agent, an ultraviolet-ray shielding ingredient were studied.

TABLE 5

|  | Present invention | | | | | |
|---|---|---|---|---|---|---|
| Composition | 2 | 4 | 5 | 6 | 7 | 8 |
| (1)beeswax | 6.0 | 6.0 | 6.0 | 6.0 | 6.0 | 6.0 |
| (2)cetanol | 5.0 | 5.0 | 5.0 | 5.0 | 5.0 | 5.0 |
| (3)reduced lanolin | 5.0 | 5.0 | 5.0 | 5.0 | 5.0 | 5.0 |
| (4)squalan | 30.0 | 30.0 | 30.0 | 30.0 | 30.0 | 30.0 |
| (5)lipophilic glyceryl monostearate | 4.0 | 4.0 | 4.0 | 4.0 | 4.0 | 4.0 |
| (6)polyoxyethylene sorbitan monolaulate (20 E.O.) | 2.0 | 2.0 | 2.0 | 2.0 | 2.0 | 2.0 |
| (7)50% ethyl alcohol extract of *Pueraria mirifica* | 5.0 | 5.0 | 5.0 | 5.0 | 5.0 | 5.0 |
| (8)placenta extract | — | 1.0 | — | — | — | — |
| (9)L-ascorbyl magnesium phosphate | — | — | 3.0 | — | — | — |
| (10)natural vitamine E | — | — | — | 0.1 | — | — |
| (11)dipotasium glycyrrhizinate | — | — | — | — | 0.5 | — |
| (12)2-ethylhexyl p-methoxy cinnamate | — | — | — | — | — | 5.0 |
| (13)antiseptics | q.s. | q.s. | q.s. | q.s | q.s. | q.s. |
| (14)perfume | q.s. | q.s. | q.s. | q.s. | q.s. | q.s. |
| (15)purified water | balance | balance | balance | balance | balance | balance |
| Whitening effect — effective | 10 | 12 | 14 | 12 | 14 | 13 |
| — slightly effective | 4 | 3 | 1 | 2 | 0 | 1 |
| — null | 1 | 0 | 0 | 1 | 1 | 1 |

(7)product by Reference example 1
(8)product by NICHIREI CORP.
(9)product by NIKKO CHEMICALS COMPANY
(10)product by EISAI CO.LTD.
(11)product by MARUZEN PHARMACY COMPANY
(12)product by BASF COMPANY (Process)
A. The components (1)–(6), (10), (12) and (13) were mixed. This mixture was heated and kept to 70° C.
B. A part of the component (15) was heated and kept to 70° C.

C. (B) part was added to (A) part. The components (7)–(8), (9) dissolved with remainder of (15), (11) and (14) were mixed and added to the mixture. The cream was obtained by cool.

(Test Method)

15 panels of 27–54 years old women were joined to the test for one subject cream. Twice in a day, in the morning and night, they applied proper quantity of subject cream to their faces after washing for 12 weeks. The whitening effect by application was evaluated by the following standard.

(Evaluation standard)

| <Evaluation> | <contents> |
| --- | --- |
| Effective | Dark of skin becomes inconspicuous. |
| Slightly Effective | Dark of skin becomes a little inconspicuous. |
| Null | No change with before use |

By applying the external preparations compounding the 50% ethyl alcohol extract of *Pueraria mirifica* on skin, it is possible to prevent or improve "dark" of skin and make skin beautiful as shown in TABLE 5.

Furthermore, the external preparations, including the 50% ethyl alcohol extract of *Pueraria mirifica* in combination with a whitening agent, an anti-oxidant, an anti-inflammation agent and an ultraviolet-ray shielding ingredient, show excellent prevention and improvement effect of "dark" of skin and make skin beautiful comparing with the case of the external preparation including 50% ethyl alcohol extract of *Pueraria mirifica* only.

ANTI-AGING TEST-1

Cell Activation Test by Cell Culturing (1)

Cell activation test was conducted by using cell of fibroblast NB1RGB of human new-born baby origin. Namely, DMEM culture media including 10% phosphate-buffered saline were taken to 24 holes laboratory dishes in a proper quantity. Fibroblast NB1RGB was inoculated to these and stored in 37° C., 5% carbon dioxide concentration. Next morning, the culture medium was exchanged to DMEM including 1% phosphate-buffered saline. The purified water extract, the 50% ethyl alcohol solution extract and the ethyl alcohol extract of *Pueraria mirifica* obtained by Reference example 1 were added to the culture mediums so the final concentration as to be 0 (a contrast) 1, 10 and 100 μg/ml, and mixed. The culture mediums were exchanged after the incubation of 4 days and the solutions same to the first were added. Next morning, the culture mediums were eliminated. The cell was retrieved after washing with phosphate buffer solution. The cell number of fibroblast NB1RGB grown in the each extracts was evaluated as a cell growth rate in comparison with the contrast. As a comparative example, soybean extract, which has already been known as a cell activator, was used, and same test was carried out. TABLE 6 shows the result.

(Evaluation Standard)

The cell numbers in the extracts obtained by Reference example 1 were compared with the cell number of the comparative example (soybean extract) and also contrast (additive-free). The cell activation effect was evaluated as cell growth rate. Also, the cell number counted by using an erythrocytometer.

TABLE 6

| EXTRACT | Concentration (μg/ml) | | |
| --- | --- | --- | --- |
| | 1 | 10 | 100 |
| (1) purified water extract | 110% | 145 | 123 |
| (2) 50% ethyl alcohol extract | 119 | 193 | 151 |
| (3) ethyl alcohol extract | 102 | 116 | 136 |
| soybeans extract | 101 | 111 | 108 |

(1)–(3): Product by Reference example 1
Soybean extract: Product by Reference example 4

It was clearly understood from TABLE 6, that the extracts of *Pueraria mirifica* have high cell activation ability to fibroblast NB1RGB of the human new-born baby origin. Accordingly, said extracts show extremely excellent anti-aging effect, by applying on skin as a cell activation component. Also, it can improve the wrinkle, slack of the skin caused by aging, ultraviolet rays exposure etc. effectively.

ANTI-AGING TEST-2

Cell Activation Test by Cell Culturing (2)

The subjects were replaced with the extract by warmed purified water and extract of warmed 50% ethyl alcohol solution obtained by Reference example 2. The other procedure is same to TEST-1. TABLE 7 shows the result.

TABLE 7

| EXTRACT | Concentration (μg/ml) | | |
| --- | --- | --- | --- |
| | 1 | 10 | 100 |
| (1) purified water extract (warmed) | 103% | 114 | 144 |
| (2) 50% ethyl alcohol extract (warmed) | 100 | 141 | 182 |
| soybeans extract | 101 | 111 | 108 |

(1), (2): Product by Reference example 2
Soybean extract: Product by Reference example 4

EXAMPLE 2-1

Anti-Aging Cream

The creams were prepared with the composition shown in TABLE 8 and also the following process. The wrinkle improvement effect of *Pueraria mirifica* was studied. TABLE 8 shows the result.

TABLE 8

| Composition | Present invention | | | Comparison | |
| --- | --- | --- | --- | --- | --- |
| | 1 | 2 | 3 | 1 | 2 |
| (1)beeswax | 6.0 | 6.0 | 6.0 | 6.0 | 6.0 |
| (2)cetanol | 5.0 | 5.0 | 5.0 | 5.0 | 5.0 |
| (3)reduced lanolin | 5.0 | 5.0 | 5.0 | 5.0 | 5.0 |
| (4)squalan | 30.0 | 30.0 | 30.0 | 30.0 | 30.0 |
| (5)lipophilic glyceryl monostearate | 4.0 | 4.0 | 4.0 | 4.0 | 4.0 |
| (6)polyoxyethylene sorbitan monolaulate (20E.O.) | 2.0 | 2.0 | 2.0 | 2.0 | 2.0 |
| (7)purified water extract of *Pueraria mirifica* | 5.0 | — | — | — | — |
| (8)50% ethyl alcohol extract of *Pueraria mirifica* | — | 5.0 | — | — | — |

TABLE 8-continued

|  | Present invention | | | Comparison | |
|---|---|---|---|---|---|
| Composition | 1 | 2 | 3 | 1 | 2 |
| (9)ethyl alcohol extract of *Pueraria mirifica* | — | — | 5.0 | — | — |
| (10)Vitamin A palmitate | | | | 5.0 | — |
| (11)antiseptics | q.s. | q.s. | q.s. | q.s. | q.s. |
| (12)perfume | q.s. | q.s. | q.s. | q.s. | q.s. |
| (13)purified water | balance | balance | balance | balance | balance |
| Wrinkle improving effect: effective | 12 | 13 | 14 | 5 | 0 |
| slightly effective | 5 | 5 | 4 | 10 | 2 |
| null | 3 | 2 | 2 | 5 | 18 |

(7)–(9)product by Reference example 1
(10)product by JAPAN ROCHE COMPANY (Process)

A. The components (1)–(6), (10) and (11) were mixed, heated and kept to 70° C.

B. A part of the component (13) was heated and kept to 70° C.

C. Part (B) was added to Part (A). The components (7)–(9), and (12) dissolved by other part of (13) were mixed and cooled to obtain the cream.

(Test Method)

20 panels of 35–59 years old women were joined to the test for one subject cream. Twice in a day, in the morning and night, they applied proper quantity of subject cream to their faces after washing for 12 weeks. The wrinkle improving effect by application was evaluated by the following standard.

(Evaluation standard)

| <Evaluation> | <contents> |
|---|---|
| Effective | Wrinkle of skin becomes inconspicuous. |
| Slightly Effective | Wrinkle of skin becomes inconspicuous a little. |
| Null | No change with before use |

By applying the external preparations (creams) compounding the purified water extract, the 50% ethyl alcohol extract and the ethyl alcohol extract of *Pueraria mirifica* on skin, it is possible to prevent or improve wrinkle of skin and make skin beautiful with tension, as shown in TABLE 8.

EXAMPLE 2-2

Anti-Aging Cream

The creams were prepared in accordance with composition shown in TABLE 9 and following process. An wrinkle improving effect of creams which included 50% ethyl alcohol extract of *Pueraria mirifica* in combination with a cell activation agent, an anti-oxidant, a humectant and an ultraviolet-ray shielding ingredient was studied. TABLE 9 shows the result.

TABLE 9

|  | Present invention | | | | | |
|---|---|---|---|---|---|---|
| Composition | 2 | 4 | 5 | 6 | 7 | 8 |
| (1)beeswax | 6.0 | 6.0 | 6.0 | 6.0 | 6.0 | 6.0 |
| (2)cetanol | 5.0 | 5.0 | 5.0 | 5.0 | 5.0 | 5.0 |
| (3)reduced lanolin | 5.0 | 5.0 | 5.0 | 5.0 | 5.0 | 5.0 |
| (4)squalan | 30.0 | 30.0 | 30.0 | 30.0 | 30.0 | 30.0 |
| (5)lipophilic glyceryl monostearate | 4.0 | 4.0 | 4.0 | 4.0 | 4.0 | 4.0 |
| (6)polyoxyethylene sorbitan monolaulate (20 E.O.) | 2.0 | 2.0 | 2.0 | 2.0 | 2.0 | 2.0 |
| (7)50% ethyl alcohol extract of *Pueraria mirifica* | 5.0 | 5.0 | 5.0 | 5.0 | 5.0 | 5.0 |
| (8)placenta extract | — | 1.0 | — | — | — | — |
| (9)Vitamine A acetate | — | — | 3.0 | — | — | — |
| (10)natural vitamine E | — | — | — | 0.1 | — | — |
| (11)hydrogenated soybean phospholipid | — | — | — | — | 0.5 | — |
| (12)2-ethylhexyl p-methoxy cinnamate | — | — | — | — | — | 5.0 |
| (13)antiseptics | q.s. | q.s. | q.s. | q.s | q.s. | q.s. |
| (14)perfume | q.s. | q.s. | q.s. | q.s. | q.s. | q.s. |
| (15)purified water | balance | balance | balance | balance | balance | balance |
| Wrinkle improving effect: effective | 13 | 18 | 19 | 15 | 16 | 14 |
| slightly effective | 5 | 2 | 1 | 4 | 3 | 4 |
| null | 2 | 0 | 0 | 1 | 1 | 2 |

(7)product by Reference example 1
(8)product of NICHIREI CORP.
(9)product of JAPAN ROCHE COMPANY
(10)product of EISAI CO.LTD.
(11)product of NIKKO CHEMICALS COMPANY
(12)product of BASF COMPANY (Process)

A. The components (1)–(6) and (9)–(13) were mixed. This mixture was heated and kept to 70° C.

B. A part of the component (15) was heated and kept to 70° C.

C. (B) part was added to (A) part. The components (7)–(8), (14) dissolved with remainder of (14) were mixed and added to the mixture. The cream was obtained by cool.

(Test Method)

20 panels of 35–59 years old women were joined to the test for one subject cream. Twice in a day, in the morning and night, they applied proper quantity of subject creams to their faces after washing for 12 weeks. The wrinkle improving effect by application was evaluated by the following standard.

(Evaluation standard)

| <Evaluation> | <contents> |
| --- | --- |
| Effective | Wrinkle of skin becomes inconspicuous. |
| Slightly Effective | Wrinkle of skin becomes inconspicuous a little. |
| Null | No change with before use |

By applying the external preparations compounding the 50% ethyl alcohol extract of *Pueraria mirifica* on skin, it is possible to prevent or improve "dark" of skin and make skin beautiful with tension as shown in TABLE 8.

Furthermore, the external preparations including the 50% ethyl alcohol extracts of *Pueraria mirifica* in combination with a cell activation agent, an anti-oxidant, a humectant and an ultraviolet-ray shielding ingredient show excellent prevention and improvement effect of wrinkle of skin and make skin beautiful with tension, comparing with the case of the external preparations including 50% ethyl alcohol extracts of *Pueraria mirifica* only.

The following compounding examples are cosmetics for whitening and anti-aging according to the present invention.

Compounding Example 1

Lotion

The lotion was prepared by the following composition and process.

| (Composition) | (wt %) |
| --- | --- |
| (1) glycerol | 5.0 |
| (2) 1,3-butylene glycol | 6.5 |
| (3) polyoxyethylene (20 E. O.) sorbitan monolaurate | 1.2 |
| (4) ethyl alcohol | 8.0 |
| (5) purified water extract of *Pueraria mirifica* *1 | 1.0 |
| (6) antiseptics | q.s. |
| (7) perfume | q.s. |
| (8) purified water | balance |

*1 manufactured by Reference example 1.

(Process)

A. The components (3), (4), (6) and (7) were mixed and dissolved.
B. The components (1), (2), (5) and (8) were mixed and dissolved.
C. Part (A) and part (B) were mixed homogeneously, and the lotion was obtained.

The product according to Compounding example 1 is excellent in stability with time. The lotion is effective for preventing "Dark" of skin, brown spot and freckle of skin by sunburn. Also, the product improved "wrinkle" and slack of skin depend on aging and make skin beautiful with a transparent impression and tension.

Compounding Example 2

Milky Lotion for Whitening

The milky lotion was prepared by the following composition and process.

| (Composition) | (wt %) |
| --- | --- |
| (1) polyoxyethylene (10 E. O.) sorbitan monostearate | 1.0 |
| (2) polyoxyethylene (60 E. O.) sorbitol tetraoleate | 0.5 |
| (3) glyceryl monostearate | 1.0 |
| (4) stearic acid | 0.5 |
| (5) behenyl alcohol | 0.5 |
| (6) squalane | 8.0 |
| (7) 50% ethyl alcohol extract extract of *Pueraria mirifica* *1 | 4.0 |
| (8) placenta *2 | 5.0 |
| (9) antiseptics | 0.1 |
| (10) carboxyvinyl polymer | 0.1 |
| (11) sodium hydroxide | 0.05 |
| (12) ethyl alcohol | 5.0 |
| (13) purified water | balance |
| (14) perfume | q.s. |

*1 manufactured by Reference example 1.
*2 product of NICHIREI CORP..

(Process)

A. The components (11)–(13) were mixed, heated and kept to 70° C.
B. The components (1)–(6) and (9) were mixed, heated and kept to 70° C.
C. Part (A) was added to Part (B). The mixture was mixed and emulsified homogeneously.
D. The components (7), (8), (10) and (14) were added to Part (C) after cooling. The milky lotion was obtained by homogeneously mixed The product according to Compounding example 2 was excellent in stability with time and anti-aging effect. The milky lotion is effective for preventing "Dark" of skin, brown spot and freckle of skin by sunburn and make skin beautiful with a transparent impression.

Compounding Example 3

Ointment

The ointment was prepared by the following composition and process.

| (Composition) | (wt %) |
| --- | --- |
| (1) stearic acid | 18.0 |
| (2) cetanol | 4.0 |
| (3) triethanolamine | 2.0 |
| (4) glycerol | 5.0 |
| (5) ethyl alcohol extract of *Pueraria mirifica* *1 | 1.0 |
| (6) dipotassium glycyrrhizinate *2 | 0.5 |
| (7) dl-alpha-tocopherol acetate *3 | 0.2 |
| (8) purified water | balance |

*1 manufactured by Reference example 1.
*2 Product of MARUZEN PHARMACY COMPANY
*3 Product of Eisai Co., Ltd.

(Process)

A. The components (3), (4) and (8) were mixed, heated and kept to 75° C.
B. The components (1), (2) and (7) were mixed, heated and kept to 75° C.
C. Part (A) is gradually added to Part (B).
D. The components (5) and (6) dissolved by a reminder of component (8) were added to Part (C) while cooling. The ointment was so obtained.

The product according to Compounding example 3 was excellent in stability with time. Applying the ointment prevented "Dark" of skin, brown spot and freckle of skin by sunburn. The product also improved "wrinkle" and slack of skin depend on aging and make skin beautiful with a transparent impression and tension.

Compounding Example 4

Pack

The pack was prepared by the following composition and process.

| (Composition) | (wt %) |
|---|---|
| (1) polyvinyl alcohol | 20.0 |
| (2) ethyl alcohol | 20.0 |
| (3) glycerol | 5.0 |
| (4) kaolin | 6.0 |
| (5) purified water extract of *Pueraria mirifica* *1 | 1.0 |
| (6) ethyl alcohol extract of *Pueraria mirifica* *1 | 0.2 |
| (7) antiseptics | 0.2 |
| (8) perfume | 0.1 |
| (9) purified water | balance |

*1 manufactured by Reference example 1.

(Process)
A. The components (1), (3), (4) and (9) were mixed and heated to 70° C., and agitated.
B. The components (2) and (7) were mixed.
C. Part (B) was added to Part (A), mixed and cooooled. The pack was obtained by adding the components (5), (6) and (8) to the mixture and dispersing homogeneously.

The product according to Compounding example 4 was excellent in stability with time. Applying the pack prevented "Dark" of skin, brown spot and freckle of skin by sunburn. The product also improved "wrinkle" and slack of skin depend on aging and make skin beautiful with a transparent impression and tension.

Compounding Example 5

Liquid Foundation for Whitening

The liquid foundation was prepared by the following composition and process.

| (Composition) | (wt %) |
|---|---|
| (1) lanolin | 7.0 |
| (2) liquid paraffin | 5.0 |
| (3) stearic acid | 2.0 |
| (4) cetanol | 1.0 |
| (5) 2-ethylhexyl p-methoxy cinnamate | 3.0 |
| (6) glycerol | 5.0 |
| (7) triethanolamine | 1.0 |
| (8) carboxymethylcellulose | 0.7 |
| (9) purified water | balance |
| (10) titanium oxide | 8.0 |
| (11) micronized particle titanium oxide | 2.0 |
| (12) zinc oxide | 5.0 |
| (13) mica | 15.0 |
| (14) talc | 6.0 |
| (15) coloring pigment | 6.0 |
| (16) 50% ethyl alcohol extract of *Pueraria mirifica* *1 | 0.01 |
| (17) coix seed extract *2 | 0.5 |
| (18) perfume | q.s. |

*1 manufactured by Reference example 1.
*2 manufactured by Reference example 3.

(Process)
A. The components (1)~(5) were mixed and dissolved.
B. The components (10)~(15) were added to Part (A). The mixture was mixed homogeneously and kept to 70° C.
C. The components (6)~(9) were dissolved homogeneously and kept to 70° C.
D. Part (C) was added to Part (B). The mixture was emulsified homogeneously.
E. Part (D) was cooled. The components (16)~(18) were added to Part (D). The liquid foundation was so obtained.

The liquid fountation according to Compounding example 5 was excellent in stability with time and anti-aging. The product is effective to prevent "Dark" of skin, brown spot and freckle of skin by sunburn.

Compounding Example 6

Milky Lotion

| Compounding example 6 Milky lotion | |
|---|---|
| (Prescription) | (wt %) |
| (1) polyoxy ethylene (10 E. O.) sorbitan monostearate | 1.0 |
| (2) polyoxy ethylene (60 E. O.) sorbitol tetraoleate | 0.5 |
| (3) glyceryl monostearate | 1.0 |
| (4) stearic acid | 0.5 |
| (5) behenyl alcohol | 0.5 |
| (6) squalane | 8.0 |
| (7) hydrogenated soybean phospholipid *1 | 0.5 |
| (8) retinol palmitate *2 | 0.5 |
| (9) 50% ethyl alcohol extract of *Pueraria mirifica* *3 | 4.0 |
| (10) placenta extract *4 | 5.0 |
| (11) antiseptics | 0.1 |
| (12) carboxy vinyl polymer | 0.1 |
| (13) sodium hydroxide | 0.05 |
| (14) ethyl alcohol | 5.0 |
| (15) purified water | balance |
| (16) perfume | q.s. |

*1 Product of NIKKO CHEMICALS COMPANY
*2 Product of JAPAN ROCHE COMPANY
*3 manufactured by Reference example 1.
*4 Product of NICHIREI CORP.

(Process)
A. The components (13)~(15) were mixed, heated and kept to 70° C.
B. The components (1)~(8) and (11) were mixed, heated and kept to 70° C.
C. Part (A) was added to Part (B). The mixture was mixed and emulsified homogeneously.
D. Part (C) was cooled. The components (9), (10), (12) and (16) were added to Part (C). The milky lotion was obtained by mixing homogeneously.

The product according to Compounding example 6 was excellent in stability with time and whitening effect. The product also improved "wrinkle" and slack of skin caused by aging and make skin beautiful with tension.

Compounding Example 7

Liquid Foundation

| Compounding example 7 Liquid foundation: | |
|---|---|
| (Prescription) | (wt %) |
| (1) lanolin | 7.0 |
| (2) liquid paraffin | 5.0 |
| (3) stearic acid | 2.0 |
| (4) cetanol | 1.0 |
| (5) ascorbyl tetra isopalmitate *1 | 2.0 |
| (6) 2-ethylhexyl p-methoxy cinnamate *2 | 3.0 |

-continued

Compounding example 7 Liquid foundation:

| (Prescription) | (wt %) |
|---|---|
| (7) glycerol | 5.0 |
| (8) triethanolamine | 1.0 |
| (9) carboxymethylcellulose | 0.7 |
| (10) purified water | balance |
| (11) titanium oxide | 8.0 |
| (12) micronized particle titanium oxide | 2.0 |
| (13) zinc oxide | 5.0 |
| (14) mica | 15.0 |
| (15) talc | 6.0 |
| (16) coloring pigment | 6.0 |
| (17) 50% ethyl alcohol extract of Pueraria mirifica *3 | 0.01 |
| (18) estradiol *4 | 0.5 |
| (19) perfume | q.s. |

*1 Product of BASF COMPANY
*2 Product of NIKKO CHEMICALS COMPANY
*3 manufactured by Reference example 1.
*4 Product of Diosynth B.V.

(Process)
A. The components (1)~(6) were mixed and dissolved.
B. The components (11)~(16) were added to Part (A). The mixture was mixed homogeneously and kept to 70° C.
C. The components (7)~(10) were dissolved homogeneously and kept to 70° C.
D. Part (C) was added to Part (B) and emulsified homogeneously.
E. Part (D) was cooled. The components (17)~(19) were added to Part (D). The liquid foundation was so obtained.

The liquid foundation according to Compounding example 7 was excellent in stability with time and whitening effect. The product also improved "wrinkle" and slack of skin caused by aging.

As mentioned above, the external preparation for skin according to the present invention includes the extract of Pueraria mirifica which has inhibition effect for melanine formation. Therefore the present invention is effective for inhibition of pigmentation, and improvement and prevention of "dark" of skin darkening, brown spots, freckles, etc. caused by sunburn.

The external preparation for skin including the Pueraria mirifica extract has also anti-aging effect. The invention is effective for improving wrinkle and slack of skin by aging and ultraviolet rays exposure.

Furthermore, the external preparation including the extract of Pueraria mirifica in combination with the active ingredient such as a whitening agent, an anti-oxidant, an anti-inflammation agent, and ultraviolet-ray shielding ingredient etc., shows more excellent whitening effect comparing with the case where said extract is compounded alone.

Also, the external preparation for skin of this invention including the extract of Pueraria mirifica in combination with the active ingredient such as a cell activation agent, an anti-oxidant, a humectant, an ultraviolet-ray shielding ingredient etc. shows more excellent anti-aging effect.

We claim:
1. A external composition for skin comprising, as an essential ingredient, a liquid extract of a dried root lump of Pueraria mirifica;
wherein said liquid extract comprises an extraction solvent which is at least one selected from the group consisting of water, lower alcohol, liquid polyhydric alcohol; and
wherein said external composition for skin contains 0.00001 to 5 wt % of said liquid extract of said dried root lump of Pueraria mirifica as dried solid in the composition.

2. The external composition for skin according to claim 1, wherein the liquid extract of the dried root lump of Pueraria mirifica is a melanine formation inhibition agent.

3. The external composition for skin according to claim 2, further comprising one or more active ingredient selected from the group consisting of a melanine formation inhibition agent, an anti-oxidant, an anti-inflammation agent, and an untraviolet-ray shielding ingredient.

4. The external composition for skin according to claim 3, wherein said melanine formation inhibition agent is selected from the group consisting of vitamin C, derivatives and salts of vitamin C, placenta extract, licorice extract, coix seed extract, scutellaria root extract, and seaweed extract.

5. The external composition for skin according to claim 3, wherein the antioxidant is selected from the group consisting of vitamin E, derivatives and salts of vitamin E, ginseng extract, astaxanthine, balm mint extract, and Alnus firma Siebold, et Zucc. extract.

6. The external composition for skin according to claim 3, wherein the anti-inflammation agent is selected from the group consisting of glycyrrhizinic acid, glycyrrhetinic acid, derivatives and salts of glycyrrhizinic acid and glycyrrhetinic acid, aloe extract, beefsteak plant extract, mugwort extract and matricaria extract.

7. The external composition for skin according to claim 3, wherein the ultraviole-ray shielding ingredient is selected from the group consisting of 2-ethyhexyl p-methoxy cinnamate, oxybenzone, 4-tert-butyl-4'methoxydibenzoylmethane, titanium oxide, micronized particle titanium oxide and zinc oxide.

8. An anti-aging composition for skin comprising, as an anti-aging ingredient, the liquid extract of claim 1.

9. The anti-aging composition for skin according to claim 8, further comprising one or more active ingredient selected from the group consisting of a cell activation agent, an anti-oxidant, an anti-inflammation agent, a humectant and an ultraviolet-ray shielding ingredient.

10. The anti-aging composition for skin according to claim 9, wherein the cell activation agent is selected from the group consisting of vitamin A, derivatives and salts of vitamin A, vitamin C, derivatives and salts of vitamin C, estradiol, placenta extract, yeast extract, apricot extract, lime extract, raspberry extract, asparagus extract, almond extract, soybean extract, centella extract, tomato extract, malt root extract and seaweed extract.

11. The anti-aging composition for skin according to claim 9, wherein the anti-oxidant is selected from the group consisting of vitamin B, derivatives and salts of vitamin B, vitamin E, derivatives and salts of vitamin E, dibutylhydroxytoluene, dibutylhydroxyanisol, mannitol, carotenoid, quercetin, quercitol, ginkgo extract, flavonoid, saxifrage extract, Siberian ginseng extract, ginseng extract, and Alnus firma Siebold. et Zucc. extract.

12. The anti-aging composition for skin according to claim 9, wherein said humectant is selected from the group consisting of an amino acid, derivatives and salts of amino acid, mucopolysaccharide, derivatives and salts of mucopolysaccharide, phospholipid, derivatives of phospholipid, sweet hydrangea leaf extract, aloe extract, cactus extract, coltsfoot extract, quince seed extract, glycerol, and 1,3-butylene glycol.

13. The anti-aging composition for skin according to claim 9, wherein said ultraviolet-ray shielding ingredient is selected from the group consisting of 2-ethylhexyl p-methoxy cinnamate, oxybenzone, and 4-tert-butyl-4'-methoxy dibenzoylmethane, titanium oxide, micronized particle titanium oxide and zinc oxide.

14. The external composition for skin according to claim 1, wherein said lower alcohol is methyl alcohol or ethyl alcohol.

15. The external composition for skin according to claim 1, wherein said polyhydric alcohol is glycerol, propylene glycol or 1,3-butylene glycol.

16. The external composition for skin according to claim 1, wherein said dried root lump of *Pueraria mirifica* is extracted in said extraction solvents at room temperature for about 1 to 5 days; said extracted being filtered; said filtrate being stayed at room temperature for aging; said aging filtrate being filtered to form the liquid extract of said dried root lump of *Pueraria mirifica*.

17. A method for preparing the external preparation for skin according to claim 1 comprising:

extracting said dried root lump of *Pueraria mirifica* in said extraction solvents at room temperature for about 1 to 5 days to obtain a liquid extract;

filtering said liquid extract to collect a filtrate;

allowing said filtrate to stay for about 1 week for aging;

filtering said aging filtrate to collect the liquid extract of said dried root lump of *Pueraria mirifica*.

18. A method for inhibiting melanine formation on skin comprising:

applying the external preparation according to claim 1 to skin to inhibit melanine formation on skin.

19. The anti-aging composition for skin according to claim 11, wherein said carotenoid is astaxanthine.

20. The anti-aging composition for skin according to claim 11, wherein said flavonoid is scutellaria root extract, or balm mint extract.

* * * * *